US012527953B2

(12) United States Patent
Tan

(10) Patent No.: US 12,527,953 B2
(45) Date of Patent: Jan. 20, 2026

(54) BEAUTY INSTRUMENT

(71) Applicant: SHENZHEN ULIKE SMART ELECTRONICS CO., LTD., Guangdong (CN)

(72) Inventor: Lijun Tan, Guangdong (CN)

(73) Assignee: SHENZHEN ULIKE SMART ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 18/818,555

(22) Filed: Aug. 28, 2024

(65) Prior Publication Data

US 2024/0416116 A1 Dec. 19, 2024

Related U.S. Application Data

(63) Continuation of application No. PCT/CN2024/072064, filed on Jan. 12, 2024.

(30) Foreign Application Priority Data

Apr. 28, 2023 (CN) ........................ 202321025281.7

(51) Int. Cl.
*A61N 1/04* (2006.01)
*A61N 1/18* (2006.01)
(Continued)

(52) U.S. Cl.
CPC ........... *A61N 1/328* (2013.01); *A61N 1/0408* (2013.01); *A61N 1/0476* (2013.01)

(58) Field of Classification Search
CPC .... A61N 1/328; A61N 1/0408; A61N 1/0476; A61N 5/0616; A61N 1/36034;
(Continued)

(56) References Cited

U.S. PATENT DOCUMENTS 6,119,038 A * 9/2000 Cook ..................... A61N 1/325 604/20
2013/0073001 A1* 3/2013 Campbell ............ A61N 5/0616 607/88
(Continued)

FOREIGN PATENT DOCUMENTS

CN 102458565 A 5/2012
CN 202207398 U 5/2012
(Continued)

OTHER PUBLICATIONS

International Search Report issued in corresponding International application No. PCT/CN2024/072064, mailed Apr. 8, 2024 (7 pages).

(Continued)

*Primary Examiner* — Carl H Layno
*Assistant Examiner* — Anh-Khoa N Dinh

(57) ABSTRACT

A beauty instrument includes a main housing and an electrode assembly. The electrode assembly is arranged in the main housing, and includes a plurality of elongated first electrodes and a plurality of dot electrodes. Each of the plurality of elongated first electrodes is at least partially exposed on the main housing, and the plurality of the first electrodes are arranged at intervals. The plurality of dot electrodes are arranged at intervals, at least part of the plurality of dot electrodes are arranged between two adjacent first electrodes in an array, and an end of each of the plurality of dot electrodes is exposed on an end of the main housing.

19 Claims, 7 Drawing Sheets

(51) Int. Cl.
*A61N 1/32* (2006.01)
*A61N 1/36* (2006.01)

(58) Field of Classification Search
CPC ............ A61N 1/322; A61N 2005/0644; A61N 1/36003; A61N 2007/0034; A61N 7/00; A61N 1/0452; A61N 1/327; A61N 1/36014; A61N 2005/0652; A61N 1/0502; A61N 1/403; A61N 1/26; A61N 1/36; A61N 1/00; A61N 1/0404; A61N 1/205; A01K 13/001; A01K 13/002; A46B 15/0006; A46B 15/0034; A46B 2200/102; A46B 2200/104; A46B 2200/1093; A46B 9/023; A61H 2201/10; A61H 2201/1685; A61H 2205/022; A61H 23/0263; A61H 7/005
See application file for complete search history.

(56) References Cited

U.S. PATENT DOCUMENTS

| | | | | |
|---|---|---|---|---|
| 2014/0207217 | A1* | 7/2014 | Lischinsky | A61N 1/0492 607/101 |
| 2014/0222026 | A1* | 8/2014 | Tenenbaum | A61N 7/00 606/131 |
| 2014/0288622 | A1* | 9/2014 | Lee | A61N 1/328 607/101 |
| 2016/0121108 | A1* | 5/2016 | Kondo | A61B 18/1402 601/2 |
| 2018/0126160 | A1 | 5/2018 | Hyun et al. | |
| 2018/0368552 | A1 | 12/2018 | Planard-Luong et al. | |
| 2019/0111252 | A1 | 4/2019 | Kang | |
| 2022/0015987 | A1 | 1/2022 | Sedic | |
| 2024/0108890 | A1* | 4/2024 | Yang | A61N 5/0616 |

FOREIGN PATENT DOCUMENTS

| | | | |
|---|---|---|---|
| CN | 203971193 | U | 12/2014 |
| CN | 209108014 | U | 7/2019 |
| CN | 113813507 | A | 12/2021 |
| CN | 113842556 | A | 12/2021 |
| CN | 215384554 | U | 1/2022 |
| CN | 114144225 | A | 3/2022 |
| CN | 217526101 | U | 10/2022 |
| CN | 217526118 | U | 10/2022 |
| CN | 115282486 | A | 11/2022 |
| CN | 115282487 | A | 11/2022 |
| CN | 217773000 | U | 11/2022 |
| CN | 218010647 | U | 12/2022 |
| CN | 218010648 | U | 12/2022 |
| CN | 218572657 | U | 3/2023 |
| CN | 218774178 | U | 3/2023 |
| CN | 115999070 | A | 4/2023 |
| CN | 116271518 | A | 6/2023 |
| CN | 219783539 | U | 10/2023 |
| CN | 219783540 | U | 10/2023 |
| CN | 219783541 | U | 10/2023 |
| JP | 2016032516 | A | 3/2016 |
| JP | 2019088373 | A | 6/2019 |
| JP | 3225776 | U | 4/2020 |
| JP | 2021027969 | A | 2/2021 |
| JP | 2021074466 | A | 5/2021 |
| KR | 101065611 | B1 | 9/2011 |
| KR | 101642248 | B1 | 7/2016 |
| WO | 2015068621 | A1 | 5/2015 |
| WO | 2022080154 | A1 | 4/2022 |

OTHER PUBLICATIONS

Written Opinion of the International Search Authority in corresponding International application No. PCT/CN2024/072064, mailed Apr. 8, 2024 (8 pages).

* cited by examiner

BEAUTY INSTRUMENT

TECHNICAL FIELD

Embodiments of the disclosure relate to the technical field of medical beauty, in particular to a beauty instrument.

BACKGROUND

A beauty instrument is an instrument for regulating and improving skin conditions, which can help people to whiten, tenderize skin, remove spots and the like, and enables the skin to be tender, glossy, and elastic. The beauty instrument stimulates and acts on the skin by way of micro-frequency current, radio frequency, ultrasonic wave, and strong light, to improve skin metabolism, contract muscles, and realize a beauty function. It can also facilitate effective ingredients in skin care products to enter deep layers of the skin so as to be more easily absorbed and utilized by the skin, and function better in beautifying.

Electrodes may be provided on a care head of the beauty instrument to care for the skin by way of micro-frequency current or radio frequency. During operations of the beauty instrument, the electrodes on the care head are in contact with and discharges to the skin, thus realizing care effect. However, the electrodes on the care head are usually block electrodes with a large area, and a large interval is kept between the block electrodes to avoid short circuit. As a result, during care, users can obviously feel parts with the electrodes and those without the electrodes on the care head, thus the care experience is not good.

SUMMARY

In view of shortcomings of related art, a beauty instrument is provided in the present disclosure, which can prevent users from obviously feeling an electrode provision area on a care head, improving discharge uniformity and care experience.

In order to achieve the above objectives, following technical scheme are adopted in the present disclosure.

A beauty instrument includes:

a main housing; and an electrode assembly provided in the main housing, the electrode assembly including:

a plurality of elongated first electrodes, each of the plurality of elongated first electrodes being at least partially exposed on the main housing, the plurality of elongated first electrodes being arranged at intervals; and a plurality of dot electrodes arranged at intervals, at least part of the plurality of dot electrodes being arranged between two adjacent first electrodes in an array, and an end of each of the plurality of dot electrodes being exposed on an end of the main housing.

In some embodiments, the plurality of dot electrodes are parallel to each other.

In some embodiments, the plurality of first electrodes include a first sub-electrode and a second sub-electrode which have opposite polarities and form an electrode pair, and at least part of the plurality of dot electrodes are arranged between the first sub-electrode and the second sub-electrode in an array.

In some embodiments, the first sub-electrode is arranged at the end of the main housing and closing to a middle area of the end of the main housing, and the second sub-electrode is arranged at an edge of the end of the main housing, and at least part of the second sub-electrode extends to a side of the main housing.

In some embodiments, the plurality of first electrodes include two second sub-electrodes, and each second sub-electrode is located at one side edge of two side edges of the main housing. The first sub-electrode is arranged between the two second sub-electrodes, and each of the two second sub-electrodes and the first sub-electrode have opposite polarities and form an electrode pair.

In some embodiments, the dot electrodes in an array are arranged between each of the two second sub-electrodes and the first sub-electrode.

In some embodiments, the electrode assembly further includes: a second electrode arranged between the two second sub-electrodes and including a first arc-shaped electrode and a second arc-shaped electrode, the first arc-shaped electrode and the second arc-shaped electrode have opposite polarities and form an electrode pair.

In some embodiments, the first arc-shaped electrode is arranged at the edge of the end of the main housing, and at least part of the first arc-shaped electrode extends to the side of the main housing.

In some embodiments, the two second sub-electrodes and the second electrode surround the plurality of dot electrodes.

In some embodiments, a part of the plurality of dot electrodes are arranged between at least one end of the first sub-electrode in a longitudinal direction and the edge of the end of the main housing.

In some embodiments, the beauty instrument further includes an operating part, connected to the main housing and configured for a user to hold and grip. An extending direction of each first electrode is perpendicular to a thickness direction of the operating part.

In some embodiments, the operating part is flat in shape, and a length direction of the operating part is perpendicular to the thickness direction of the operating part. The operating part is provided with two grip parts, and each grip part is arranged on a flat surface on one side of two sides of the operating part in the thickness direction of the operating part.

In some embodiments, each grip part includes a concave part formed on a side of the operating part, and the concave part extends along a length direction of each first electrode.

In some embodiments, the plurality of dot electrodes includes a plurality of rows of dot electrodes, and two adjacent dot electrodes among each row of dot electrodes have opposite polarities and form an electrode pair.

In some embodiments, the second electrode is disposed at an end of each first electrode along an extending direction of each first electrode.

In some embodiments, the beauty instrument further includes an operating part connected to the main housing and configured for a user to hold and grip. Each second sub-electrode of the two second sub-electrodes is arranged on one side of two sides of the main housing in a thickness direction of the operating part, the first arc-shaped electrode and the second arc-shaped electrode are located between the two second sub-electrodes and at an end of the first sub-electrode, and the first arc-shaped electrode is further away from the first sub-electrode than the second arc-shaped electrode.

In some embodiments, an area of the first arc-shaped electrode and an area of the second arc-shaped electrode are both larger than an area of the dot electrode; and/or the second arc-shaped electrode is arranged at an end of the main housing and close to the first arc-shaped electrode;

and/or the first arc-shaped electrode and the second arc-shaped electrode extend in a same direction, and the first arc-shaped electrode and the second arc-shaped electrode are arched away from the first sub-electrode; and/or the beauty instrument further includes an operating part connected to the main housing and configured for a user to hold and grip, and both the first arc-shaped electrode and the second arc-shaped electrode extend toward two sides of the operating part in a thickness direction of the operating part; and/or a connecting line of curvature centers of the first arc-shaped electrode and the second arc-shaped electrode is collinear with an extension line of the first sub-electrode; and/or the plurality of dot electrodes are arranged between the second arc-shaped electrode and the first sub-electrode.

In some embodiments, an edge of each first electrode is chamfered; and/or two ends of each first electrode in a length direction are arc-shaped; and/or an edge of each dot electrode is chamfered.

In some embodiments, an edge of the second electrode is chamfered; and/or two ends of the second electrode in a length direction are arc-shaped.

According to the present disclosure, the elongated first electrodes act on the skin in a large area and discharge, and the dot electrodes between the elongated first electrodes are used to uniformly discharge on the skin in the area between the first electrodes, so that user is prevented from obviously feeling the electrode provision area on the care head. In such a way, a caring area of the electrodes of the beauty instrument is increased, and care experience and efficiency are also improved. Further, different electrodes can act on the skin in different areas, thereby further expanding application scenes and meeting care needs of different skin areas.

Figure 1:
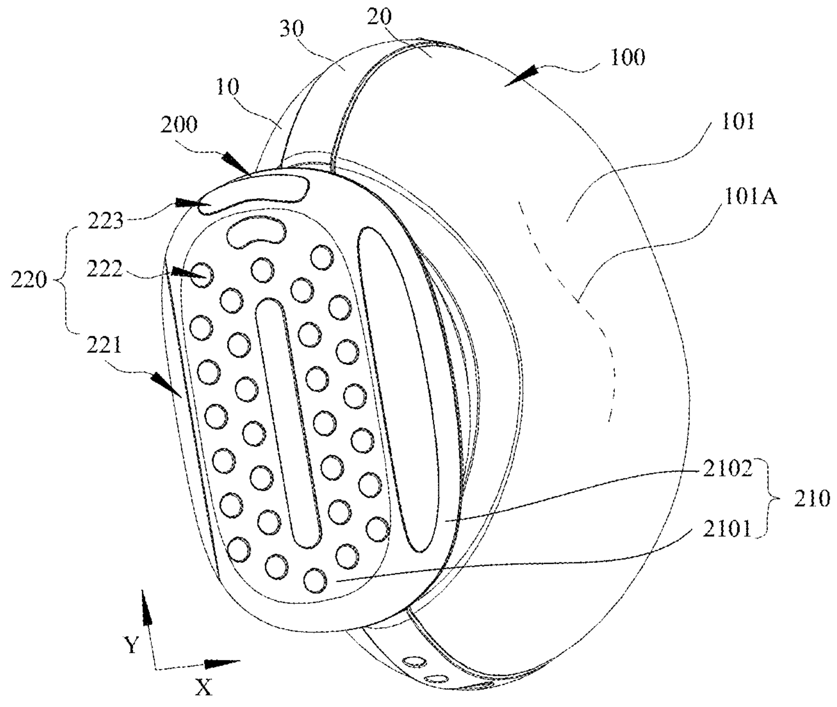
FIG. 1 is a schematic structural view of a beauty instrument according to an embodiment of the present disclosure.

Realization of the objects, functional characteristics and advantages of the disclosure will be further explained in combination with embodiments and with reference to attached figures.

DETAILED DESCRIPTION OF THE EMBODIMENTS

In this disclosure, terms “arrange”, “provide” and “connect” should be broadly understood. For example, it can be a fixedly connected, a detachably connected, or integrally constructed; it can be mechanically or electrically connected; it can be directly connected, indirectly connected through an intermediate medium, or internally communicated between two apparatus, elements or components. For those ordinary skilled in the art, the specific meanings of the above terms in this disclosure can be understood according to specific situations.

An orientation or positional relationship indicated by terms “center”, “longitudinal”, “transverse”, “length”, “width”, “thickness”, “upper”, “lower”, “front”, “rear”, “left”, “right”, “vertical”, “horizontal”, “top”, “bottom”, “inner”, “outer”, “axial”, “radial”, “circumferential” and the like is based on the orientation or positional relationship shown in the drawings, which is only for the convenience of describing the present disclosure and simplifying the description, but does not indicate or imply that the referred device or element must have a specific orientation, be constructed and operated in a specific orientation, and thus cannot be understood as limiting the present disclosure.

In addition, the terms “first” and “second” are only configured for descriptive purposes and cannot be understood as indicating or implying a relative importance, or implicitly indicating a number of indicated technical features. Therefore, the features defined with “first” and “second” can explicitly or implicitly include at least one of these features. In description of this present disclosure, “a plurality of” means at least two, such as two, three, etc., unless otherwise specifically defined.

In addition, some of the above terms can be used to indicate not only the azimuth or positional relationship, but also the other meaning. For example, the term “on” may also be used to indicate some attachment or connection relationship in some cases. For those ordinary skilled in the art, specific meanings of these terms in this application can be understood according to specific situations.

In order to make the objects, technical schemes, and advantages of the present disclosure clearer, the present disclosure will be further described in detail with reference to the drawings and examples. It should be understood that the specific embodiments described herein are only used to explain the present disclosure, and are not intended to limit the present disclosure.

Referring to FIG. 1, a beauty instrument is provided in an embodiment of the present disclosure, which includes an operating part 100 for a user to hold and grip and a performing part 200 for performing skin care. The user can hold the operating part 100 and face the performing part 200 towards skin so as to perform the skin care. For example, an electrode and/or a therapy lamp can be provided at an end of the performing part 200, and the performing part 200 can contact a skin surface and move back and forth on the skin surface, so as to achieve effect such as skin rejuvenation and beauty.

In an embodiment, the operating part 100 includes a front housing 10, a rear housing 20, and a middle housing assembly 30. The front housing 10 and the rear housing 20 are respectively fixed to the middle housing assembly 30 from one side of two opposite sides of the middle housing assembly 30, to define an accommodation for accommodating internal electrical components such as circuits and wirings.

In an embodiment, the middle housing assembly 30 may be provided with a button (not shown) that can be operated and pressed by the user, so as to realize operations of switching functions of the beauty instrument or turning on and off of the power supply, or the middle housing assembly 30 may be provided with an indicator lamp that indicates an operation state of the beauty instrument.

Figure 2:
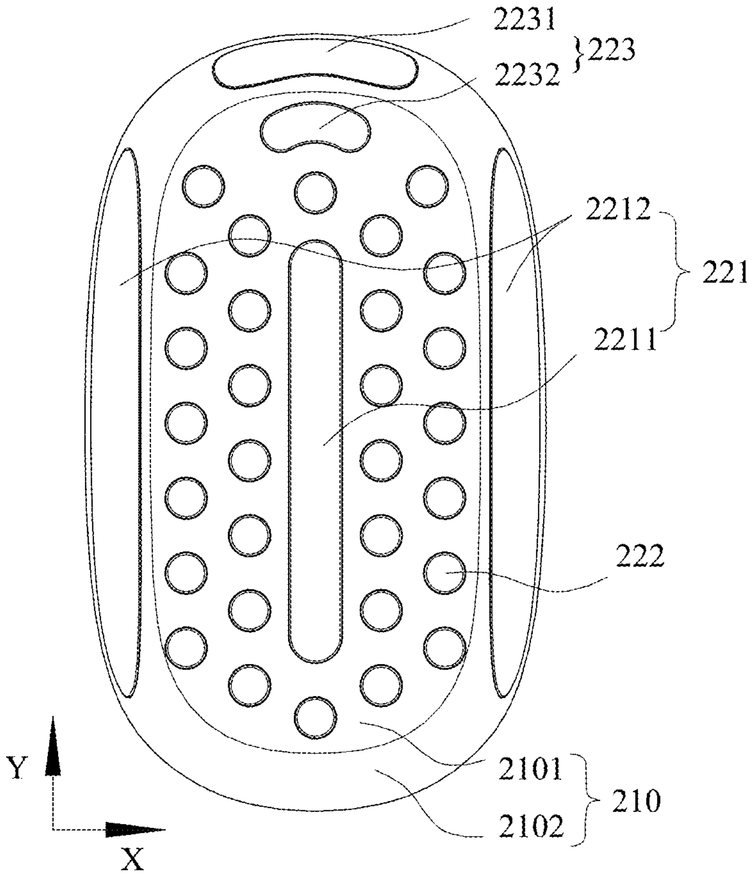
FIG. 2 shows a schematic structural view of operating parts of a beauty instrument according to an embodiment of the present disclosure.

With reference to FIGS. 1 and 2, the operating part 100 of the beauty instrument according to this embodiment includes two grip parts 101 with each being arranged on one side of two opposite sides of the operating part 100 in a thickness direction X, and the grip parts 101 are configured for being held by users. The performing part 200 includes a main housing 210 and an electrode assembly 220. The main housing 210 is connected with the operating part 100, and the electrode assembly 220 is arranged and fixed to the main housing 210. The electrode assembly 220 includes an elongated first electrode 221. The first electrode 221 is at least partially exposed on the main housing 210, and an extending direction Y of the first electrode 221 is consistent with a direction perpendicular to a thickness direction X of the operating part 100. That is, the extending direction Y of the first electrode 221 is basically perpendicular to the thickness direction X of the operating part 100, so that the two grip parts 101 are arranged at intervals in the extending direction which is basically perpendicular to the first electrode 221, which facilitates to guiding the user to move the beauty instrument along the extending direction Y of the first electrode 221. "Basically perpendicular" can be understood as vertical, or there is small deviation from a vertical state, for example with a deviation angle from the vertical direction within ±15°.

It can be understood that in this disclosure, the electrode is exposed on the main housing, which may include a situation that the electrode is convexly provided at a surface of the main housing, a situation that a surface of the electrode is flush with a surface of the main housing, or a situation that a groove is defined in the surface of the main housing, the electrode is accommodated in the groove, and the surface of the main housing protrudes from the surface of the electrode, as long as the electrode can discharge to the skin during contact between the housing and the skin.

In an embodiment, the operating part 100 is flat in shape, with a length direction perpendicular to its thickness direction. In the thickness direction of the operating part 100, each of the grip part 101 is arranged on flat surface at one side of both sides of the operating part 100. During using the beauty instrument, the user can hold the operating part 100 with one hand and push the beauty instrument back and forth along the length direction of the operating part 100 by holding the two grip parts 101. Since the extending direction Y of the first electrode 221 is basically perpendicular to the thickness direction X of the operating part 100, the first electrode 221 extends basically along the length direction of the operating part 100, so that when the beauty instrument is pushed along the skin surface, the length direction of the first electrode 221 is consistent with a moving direction of the beauty instrument, and the first electrode 221 moves on the skin surface along a pushing direction of the beauty instrument, which can reduce foreign body sensation on the skin surface of the user during operations of the beauty instrument and realize more comfortable care experience.

The operating part of the beauty instrument according to this embodiment is provided with an elongated first electrode. During use of the beauty instrument, the user holds the grip parts of the operating part and pushes the beauty instrument to move on the skin surface to perform skin care. Since the extending direction of the first electrode is basically perpendicular to the thickness direction of the operating part, the extending direction of the first electrode is consistent with the moving direction of the beauty instrument during movement of the beauty instrument, thus the user may not feel the foreign body sensation at care sites, and the elongated electrode ensures a contact area of the electrode with the skin, thus improving care efficiency and ensuring care experience. In this embodiment, a shape of the first electrode is provided to be matched with a setting of the grip part so as to guide the user to move the beauty instrument, thus fully using advantages of the strip electrode and improving the care efficiency and experience.

In an embodiment, the grip part 101 includes concave parts 101A formed on a side of the operating part 100, and each of the concave parts 101A may extend along the length direction of the first electrode 221. The grip part 101 can also be provided as a profiling concave part matched with a human hand. For example, the grip part 101 includes a first concave part corresponding to an arc contour of a human palm and a second concave part corresponding to a contour of a human knuckle. Due to provision of the profiling concave part, a contact area between a side surface of the operating part 100 and the human hand is increased, and the user can hold it more firmly.

In an embodiment, there may be more than one first electrode 221. As shown in FIG. 2, the first electrodes 221 include a first sub-electrode 2211 and a second sub-electrode 2212 arranged at intervals in the thickness direction X of the operating part 100. The first sub-electrode 2211 and the second sub-electrode 2212 have opposite polarities and form an electrode pair. Illustratively, the first electrodes 221 are parallel to each other, that is, extending directions of the first electrodes 221 are the same. When the beauty instrument moves along the skin surface, the first sub-electrode 2211 and the second sub-electrode 2212 are in contact with the skin at the same time, thus forming a loop and generating a current at a contact site with the skin, for example, a micro current or radio frequency current, to perform skin care.

In an embodiment, the electrode assembly 220 further includes a plurality of dot electrodes 222 arranged at intervals, and at least part of the dot electrodes 222 are arranged in an array between the first sub-electrode 2211 and the second sub-electrode 2212, and an end of each of the dot electrodes 222 is exposed on an end 2101 of the main housing 210. The dot electrodes 222 are configured to perform skin care by generating micro current or radio frequency current.

In an embodiment, the electrode assembly 220 includes a plurality of rows of dot electrodes 222 arranged side by side, and two adjacent dot electrodes 222 among each row of dot electrodes 222 have opposite polarities and form an electrode pair. Illustratively, the electrode assembly 220 includes a plurality of rows of dot electrodes 222 arranged along the extending direction Y of the first electrode 221, and two adjacent dot electrodes 222 among each row of dot electrodes 222 have opposite polarities and form an electrode pair. When the two adjacent dot electrodes 222 among each row of dot electrodes 222 contact the skin at the same time, they can form a loop, thereby discharging to the skin. It can be understood that formation of electrode pairs of the dot electrodes 222 is not limited to this. For example, in other embodiments, two adjacent dot electrodes 222 in a direction perpendicular to the row of the dot electrodes 222 have opposite polarities and form an electrode pair.

In an embodiment, an area of each of the dot electrodes 222 is small, but there are a larger number of dot electrodes, and a cross section of the dot electrode 222 may be circular or elliptical. Illustratively, the dot electrodes 222 output a radio frequency current for skin care. In this embodiment, a large number of dot electrodes 222 are configured to contact with the skin, thus discharging to the skin. Compared with a method of using large-area electrodes for discharging, an effective contact area between the dot electrodes 222 and the skin is larger. For example, in areas with curvature such as mandible, the electrodes in array are more conducive to contact with the skin than the large-area electrodes. Moreover, due to decentralized arrangement of the dot electrodes 222, on a premise of a same electrode area, the decentralized electrodes have a larger skin action area than the large-area electrodes, with more uniform radio frequency energy distribution. It can be understood that in other embodiments, a micro current can also be output through the dot electrode 222 for the skin care.

In an embodiment, the main housing 210 includes an end 2101 and a side 2102. The electrodes at the end 2101 of the main housing 210 can discharge to the skin with flat area, and the electrodes at the side 2102 of the main housing 210 can discharge to the local skin. The first sub-electrode 2211 is arranged at the end 2101 of the main housing 210 and closing to a middle area of the end 2101 of the main housing, and the second sub-electrode 2212 is arranged at an edge of the end 2101 of the main housing 210 and partially extends to the side 2102 of the main housing 210. When the beauty instrument is pushed along the skin surface, the first sub-electrode 2211, the second sub-electrode 2212, and the dot electrodes 222 can serve to perform skin care for large flat area, for example, by generating a micro current to act on the skin to achieve skin resurfacing effect. The second sub-electrode 2212 can serve to perform care for an uneven skin surface. For example, the second sub-electrode 2212 may be in contact with an edge of the nose to discharge to the skin around the nose.

Illustratively, the first electrodes 221 include two second sub-electrodes 2212, with each second sub-electrode 2212 being located at one side edge of two side edges of the main housing 210 in the thickness direction X of the operating part 100. The first sub-electrode 2211 is arranged between the two second sub-electrodes 2212, and each of the two second sub-electrodes 2212 and the first sub-electrode 2211 have opposite polarities and form an electrode pair. When the first sub-electrode 2211 and a corresponding second sub-electrode 2212 are in contact with the skin at the same time, they can form a loop and thus discharge to the skin. The second sub-electrodes 2212 at the two sides can serve to respectively perform care for skin in different areas, thus expanding application scenarios. In addition, dot electrodes 222 may be arranged between the second sub-electrodes 2212 at the two sides and the first sub-electrode 2211 at the middle, and the dot electrodes 222 can cooperate with the first sub-electrode 2211 and the second sub-electrode 2212 of the first electrodes 221, so that the first sub-electrode 2211 and the second sub-electrode 2212 discharge to skin at an edge of a target area, while the dot electrodes 222 discharge to skin between the first sub-electrode 2211 and the first sub-electrode 2212, thus further expanding application scenarios and meeting care needs of different skin areas.

Because the two second sub-electrodes 2212 are respectively located at two side edges of the main housing 210 in the thickness direction X of the operating part 100, a distance between the second sub-electrode 2212 and the first sub-electrode 2211 can be maximized, so that a current sensation felt by the user is weakest during the second sub-electrode 2212 and the first sub-electrode 2211 are in contact with the skin and discharging, and thus comfort of care experience is improved to a maximum extent.

Illustratively, when it needs to achieve skin tightening effect for large-area skin, the beauty instrument can operate in a pulling mode and discharge to the large-area skin. For example, in this mode, the first electrode 221 and the dot electrode 222 output a radio frequency current at the same time, or the first electrode 221 outputs a micro current, or the first electrode 221 and the dot electrode 222 output a radio frequency current at the same time for a period of time and then the first electrode 221 outputs a micro current for a period of time, and these two manners are alternately adopted to discharge to the skin.

Illustratively, when it needs to perform care for skin in a nasolabial fold area, it can be achieved by cooperation of the first electrodes 221 and the dot electrodes 222. For example, the first electrode 221 and the dot electrode 222 can be combined and configured to alternately output the micro current and the radio frequency current, so that it is not easy for users to perceive change in current.

Illustratively, when it needs to perform care for skin in different areas, it can also be achieved by cooperation of the first electrodes 221 and the dot electrodes 222. For example, the first electrode 221 and the dot electrode 222 can be combined and alternately energized with a micro current and a radio frequency current, and after care for each area for a period of time, care can be performed for another care area, and in this process, it is not easy for users to perceive change in current.

In an embodiment, the electrode assembly 220 further includes a second electrode 223, and the second electrode 223 includes a first arc-shaped electrode 2231 and a second arc-shaped electrode 2232, which have opposite polarities and form an electrode pair. Illustratively, areas of the first arc-shaped electrode 2231 and the second arc-shaped electrode 2232 are both larger than that of the dot electrode 222. When the first arc-shaped electrode 2231 and the second arc-shaped electrode 2232 are in contact with the skin at the same time, they can form a loop and thus discharge to the skin.

In an embodiment, the first arc-shaped electrode 2231 is disposed at the edge of the end 2101 of the main housing 210 and partially extends to the side 2102 of the main housing 210, and the second arc-shaped electrode 2232 is disposed at the end 2101 of the main housing 210 and closing to the first arc-shaped electrode 2231. In this way, the first arc-shaped electrode 2231 and the second arc-shaped electrode 2232 of the second electrode 223 are located at the edge of the end 2101 of the main housing 210, and can be in contact with an uneven skin surface to discharge.

Illustratively, when it needs to perform care for skin at an eye area, it can be achieved by cooperation of the first arc-shaped electrode 2231 and the second arc-shaped electrode 2232 of the second electrode 223 to be in contact with the skin to discharge. For example, by alternately outputting a micro current and a radio frequency current by the first arc-shaped electrode 2231 and the second arc-shaped electrode 2232, it is not easy for users to perceive change in current.

In an embodiment, the second electrode 223 is disposed at an end of the first electrode 221 along the extending direction Y of the first electrode 221. For example, in the thickness direction X of the operating part 100, each of the two second sub-electrodes 2212 is arranged on one side of two sides of the main housing 210, and the first arc-shaped electrode 2231 and the second arc-shaped electrode 2232 are located between the two second sub-electrodes 2212 and at an end of the first sub-electrode 2211. The first arc-shaped electrode 2231 is further away from the first sub-electrode 2211 than the second arc-shaped electrode 2232.

In an embodiment, the first arc-shaped electrode 2231 and the second arc-shaped electrode 2232 extend in a same direction, and both of them are arched away from the first sub-electrode 2211. Both the first arc-shaped electrode 2231 and the second arc-shaped electrode 2232 extend towards both sides of the operating part 100 in the thickness direction X, that is, extend towards the two sides where the second sub-electrodes 2212 are located. When user moves the beauty instrument along the extending direction Y of the first electrode 221, length directions of the first arc-shaped electrode 2231 and the second arc-shaped electrode 2232 vertically intersect with the moving direction of the beauty instrument.

Illustratively, a connecting line of curvature centers of the first arc-shaped electrode 2231 and the second arc-shaped electrode 2232 is collinear with an extension line of the first sub-electrode 2211. Dot electrodes 222 may be also provided between the second arc-shaped electrode 2232 and the first sub-electrode 2211.

In an embodiment, an edge of the first electrode 221 is chamfered, for example, rounded or beveled; and/or both ends of the first electrode 221 in the longitudinal direction are arc-shaped. In this way, foreign body sensation caused by respective electrode of the electrode assembly 220 being in contact with the skin and moving on the skin surface can be further weakened. It can be understood that other electrodes of the electrode assembly 220 can be of similar structures. For example, edges of the dot electrodes 222 and the second electrode 223 can be chamfered, and both ends of the second electrode 223 in the length direction can also be arranged in an arc shape.

Figure 3:
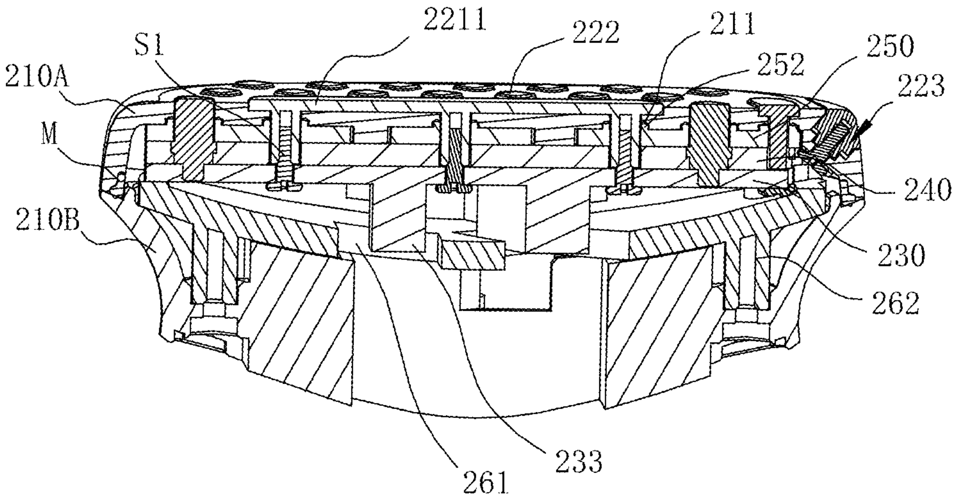
FIG. 3 shows a schematic sectional view of operating parts of a beauty instrument according to an embodiment of the present disclosure.
Figure 4:
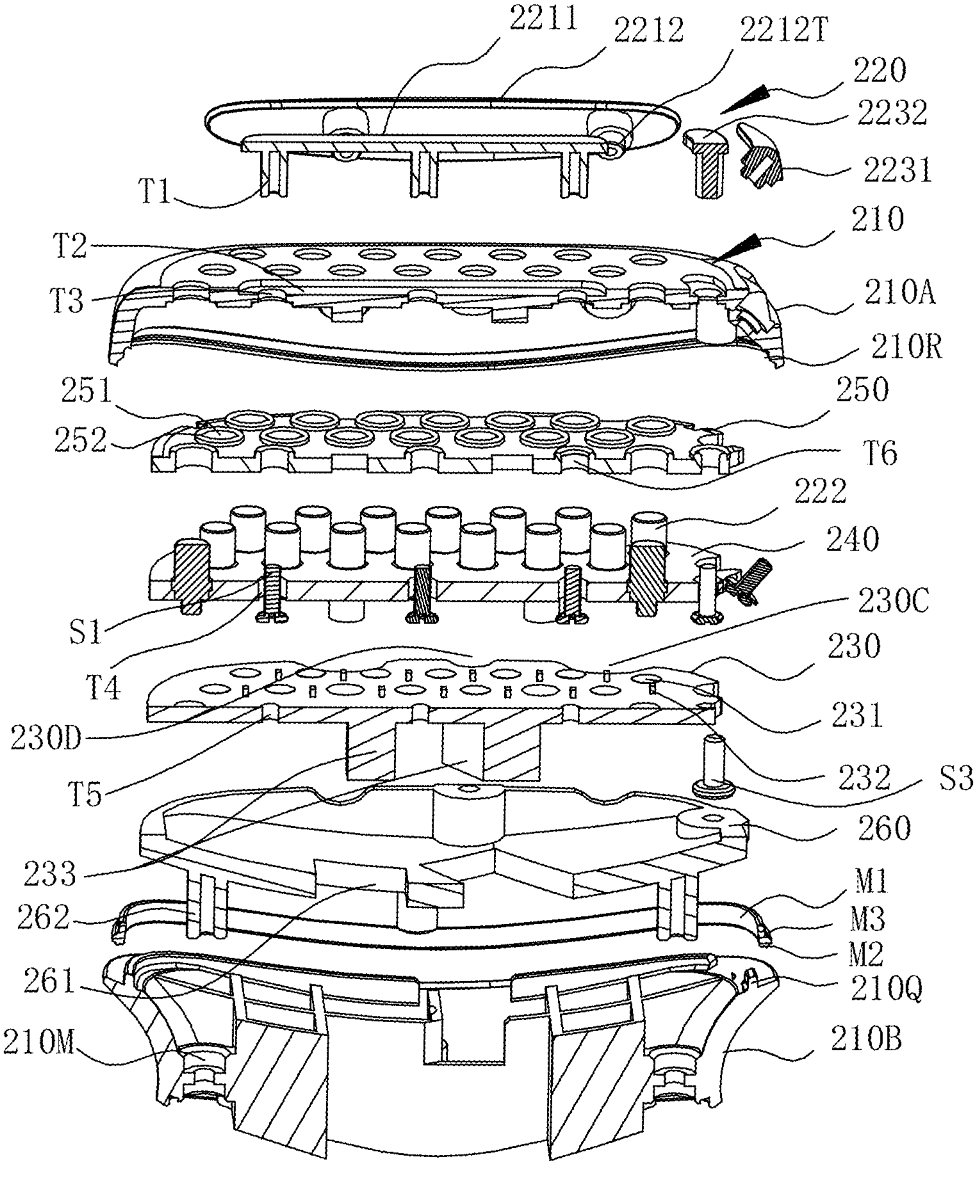
FIG. 4 shows a schematic exploded view of operating parts of a beauty instrument according to an embodiment of the present disclosure.
Figure 5:
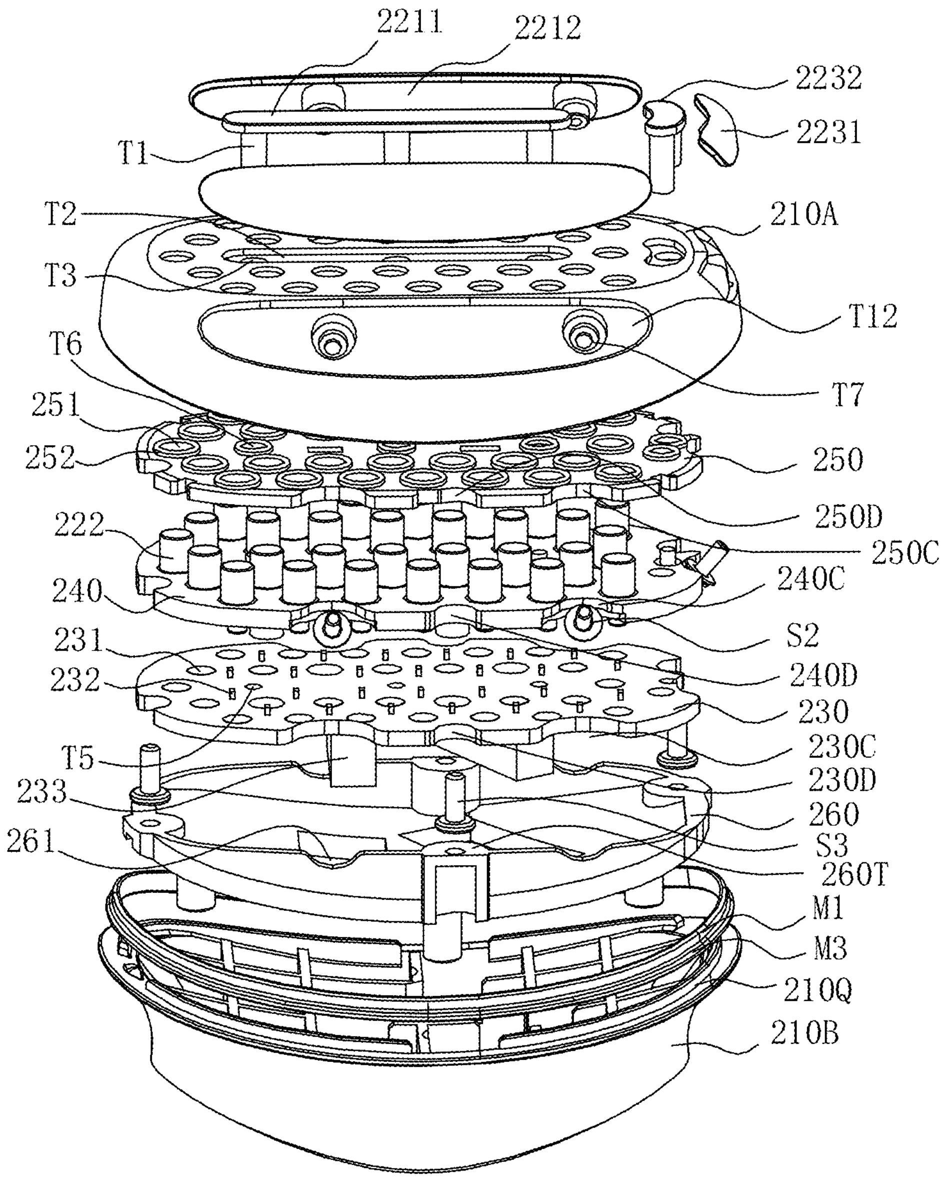
FIG. 5 shows another schematic exploded view of operating parts of a beauty instrument according to an embodiment of the present disclosure.

As shown in FIGS. 3 and 4, in an embodiment, the performing part 200 includes a circuit board 230, and the circuit board 230 is fixed in the main housing 210. A plurality of electrode contacts 231 are provided at a side of the circuit board 230 facing the electrode assembly 220. The electrode assembly 220 includes a plurality of dot electrodes 222, first ends of the plurality of dot electrodes 222 are abutted against the electrode contacts 231, and second ends of the plurality of dot electrodes 222 are exposed on the end 2101 of the main housing 210 to discharge to skin.

The second ends of the dot electrodes 222 are limited by the end 2101 of the main housing 210, and the first ends of the dot electrodes 222 are abutted against the electrode contacts 231, so as to realize a passage between the dot electrodes 222, the circuit board 230, and human skin. When two adjacent dot electrodes 222 are in contact with the human skin at the same time, the two dot electrodes 222 form a loop, so as to discharge to the skin for care. Such construction of detachable dot electrodes 222 also facilitates replacement and maintenance of the electrodes.

In an embodiment, the performing part 200 further includes an insulating substrate 240, and each of the dot electrodes 222 penetrates through and is fixed to the insulating substrate 240. In this way, during installing the dot electrodes 222, the first ends of the dot electrodes 222 can be in contact with corresponding electrode contacts 231 on the circuit board 230 only by aligning and fixing the insulating substrate 240 to the main housing 210 and the circuit board 230. By integrating the dot electrodes 222 together using the insulating substrate 240, the dot electrodes 222 can be quickly disassembled and assembled, thus disassembling and assembling steps are simplified.

In an embodiment, the dot electrodes 222 and the insulating substrate 240 are integrally formed, for example, by injection molding, which simplifies a manufacturing process and improves assembly efficiency of the beauty instrument.

In an embodiment, the performing part 200 includes a circuit board 230 fixed in the main housing 210, and a plurality of lamp beads 232 are provided at a side of the circuit board 230 facing the electrode assembly 220. Correspondingly, a region of the main housing 210 facing the lamp beads 232 is allowed to be light-transmitting, and light emitted by the lamp beads 232 passes through the main housing 210 for skin care.

In an embodiment, the performing part 200 includes both the dot electrodes 222 and the lamp beads 232, and the lamp beads 232 are arranged among the dot electrodes 222. In the performing part 200 provided with the insulating substrate 240, the insulating substrate 240 can be made of a light-transmitting material, and light emitted by the lamp beads 232 passes through the insulating substrate 240 and then passes through the main housing 210, thereby performing skin care. In this way, the insulating substrate 240 can not only be used as a fixing medium for the dot electrodes 222, but also as a light-diffusing medium for the lamp beads 232, so that the light emitted from the lamp beads 232 to the human skin is more uniform and softer, thus realizing various functions.

In an embodiment, the performing part 200 of the beauty instrument includes:

- a main housing 210;
- an electrode assembly 220 provided and fixed to the main housing 210;
- a circuit board 230 fixed in the main housing 210, a plurality of electrode contacts 231 being provided at a side of the circuit board 230 facing the electrode assembly 220; and
- an insulating substrate 240.

The electrode assembly 220 includes a plurality of dot electrodes 222, each of the plurality of dot electrodes 222 penetrates through and is fixed to the insulating substrate 240. First ends of the plurality of dot electrodes 222 are abutted against the electrode contacts 231, and second ends of the plurality of dot electrodes 222 are exposed on the main housing 210 to discharge to skin.

Because the insulating substrate 240 integrates the dot electrodes 222 together, respective dot electrode 222 does not need to be mounted on the circuit board 230 or the main housing 210 one by one, but only needs to align the insulating substrate 240 to corresponding sites on the circuit board 230 or the main housing 210 and then complete relative fixation, and in this way, the respective dot electrode 222 can be in contact with the corresponding electrode contact 231 on the circuit board 230, thus eliminating cumbersome installation steps. Moreover, because the dot electrodes 222 are fixed to the insulating substrate 240, in case the dot electrodes 222 are damaged, it is only need to replace the insulating substrate 240, which improves convenience of maintenance.

In an embodiment, the dot electrodes 222 and the insulating substrate 240 are integrally formed, for example, by injection molding, which simplifies a manufacturing process and improves assembly efficiency of the beauty instrument.

In an embodiment, a plurality of lamp beads 232 are provided at a side of the circuit board 230 facing the electrode assembly 220, and the lamp beads 232 are arranged among the dot electrodes 222. The insulating substrate 240 is made of a light-transmitting material, and a region of the main housing 210 facing the lamp beads 232 is allowed to be light-transmitting. In this way, the insulating substrate 240 can not only be used as a fixing medium for the dot electrodes 222, but also as a light-diffusing medium for the lamp beads 232, so that the light emitted from the lamp beads 232 to the human skin is more uniform and softer, thus realizing various functions.

Referring to FIGS. 3 to 7, in an embodiment, the performing part 200 may further include a sealing gasket 250. The sealing gasket 250 is arranged between the insulating substrate 240 and the main housing 210, and is provided with a plurality of first through holes 251 corresponding to the dot electrodes 222, and the second ends of the dot electrodes 222 are exposed on the main housing 210 after passing through the first through holes 251. The sealing gasket 250 is pressed against an inner surface of the end 2101 of the main housing 210 by the insulating substrate 240, and the sealing gasket 250 cooperates with the insulating substrate 240 and the end 2101 of the main housing 210 to seal an outer peripheral surface of each of the second ends of the dot electrodes 222.

The sealing gasket 250 may be made of a soft material, such as silica gel, rubber, etc., which can block external water vapor from entering the main housing 210. When the lamp beads 232 are arranged on the circuit board 230, the sealing gasket 250 is made of a light-transmitting material, and light emitted by the lamp beads 232 can pass through the sealing gasket 250.

In an embodiment, a plurality of annular flanges 252 are protruded at a surface of the sealing gasket 250 facing away from the insulating substrate 240, each of the plurality of flanges 252 is arranged around an edge of one first through hole 251. When the second end of the dot electrode 222 passes through the first through hole 251, the flange 252 is sealed at the outer peripheral surface of the second end of the dot electrode 222.

In an embodiment, the inner surface of the end 2101 of the main housing 210 is provided with a step portion 211 (as shown in FIG. 3) facing the first through holes 251, the sealing gasket 250 is attached to the inner surface of the end 2101 of the main housing 210, and each the flange 252 is embedded in the step portion 211. Illustratively, the sealing gasket 250 is elastically compressed to the inner surface of the end part of the main housing 210, with its flange 252 being embedded in the step portion 211, and its body part being closely attached to the inner surface of the end part of the main housing 210. In this way, the flange 252 can prevent water vapor from entering into the main housing 210 from the first through holes 251, and the body part of the sealing gasket 250 can prevent water vapor from entering into the main housing 210 from a gap between the sealing gasket 250 and the inner surface of the end 2101 of the main housing 210.

In an embodiment, the electrode assembly 220 includes an elongated first sub-electrode 2211, and the elongated first sub-electrode 2211 is arranged at the end 2101 of the main housing 210 and closing to a middle area of the end 2101 of the main housing 210. A first fixing post T1 is protruded from an inner surface of the first sub-electrode 2211, and the first fixing post T1 of the first sub-electrode 2211 is inserted into the main housing 210 for fixing.

Specifically, an outer surface of the main housing 210 is defined with a first mounting groove T2 and a second through hole T3 is defined in a bottom of the first mounting groove T2, the insulating substrate 240 is defined with a third through hole T4 facing the second through hole T3, and the circuit board 230 is defined with a fourth through hole T5 facing the second through hole T3. The first sub-electrode 2211 is embedded in the first mounting groove T2, and the first fixing post T1 passes through the second through hole T3 and the third through hole T4 in sequence to be connected with a first fastener S1 inserted from the fourth through hole T5.

The first mounting groove T2 may provide an accommodating and limiting space for a part of the first sub-electrode 2211 located outside the main housing 210, and the first sub-electrode 2211 partially protrudes outside the first mounting groove T2 to contact the skin. The second through hole T3 and the third through hole T4 provide a space for the first fixing post T1 of the first sub-electrode 2211 to pass through, and the fourth through hole T5 provides a space for the first fastener S1 to pass through. Illustratively, the first fixing post T1 is a stud, and the first fastener S1 is threadedly connected with the first fixing post T1.

In an embodiment, the sealing gasket 250 is defined with a fifth through hole T6 facing the second through hole T3 and the third through hole T4, and the first fixing post T1 further passes through the fifth through hole T6. In some embodiments, an annular flange 252 is provided at an edge of a surface of the fifth through hole T6 facing away from the insulating substrate 240 to seal the first fixing post T1. Illustratively, there may be a plurality of first fixing posts T1, and the plurality of first fixing posts T1 are distributed in the length direction of the first sub-electrode 2211 at intervals to cooperate with a corresponding first fastener S1 to fix different parts of the first sub-electrode 2211.

Through above arrangement, the first fastener S1 cooperates with the first fixing post T1 to fix the first sub-electrode 2211 at the end 2101 of the main housing 210, and fix the circuit board 230, the insulating substrate 240, and the sealing gasket 250 at an inner surface of the end 2101 of the main housing 210.

In an embodiment, the electrode assembly 220 further includes an elongated second sub-electrode 2212. The elongated second sub-electrode 2212 is arranged at the edge of the end 2101 of the main housing 210 and partially extends to the side 2102 of the main housing 210. A second fixing post 2212T is protruded from an inner surface of the second sub-electrode 2212 and obliquely arranged relative to the end 2101 of the main housing 210, and the second fixing post 2212T of the second sub-electrode 2212 is inserted into the main housing 210 for fixing.

In particular, the outer surface of the main housing 210 is defined with a second mounting groove T12 and a sixth through hole T7 is defined in a bottom of the second mounting groove T12, an edge of the circuit board 230 is defined with a first avoidance groove 230C, and the edge of the insulating substrate 240 is defined with a second avoidance groove 240C. The second sub-electrode 2212 is embedded in the second mounting groove T12, and the second fixing post 2212T passes through the sixth through hole T7 to be connected with a second fastener S2 provided in the first avoidance groove 230C and the second avoidance groove 240C.

The second mounting groove T12 may provide an accommodating and limiting space for a part of the second sub-electrode 2212 located outside the main housing 210, and the second sub-electrode 2212 partially protrudes outside the second mounting groove T12 to contact the skin. The sixth through hole T7 provides a space for the second fixing post 2212T of the second sub-electrode 2212 to pass through, and the second avoidance groove 240C and the first avoidance groove 230C provide an avoidance space for the second fixing post 2212T. The second fastener S2 is connected with the second fixing post 2212T and partially located in the first avoidance groove 230C. Illustratively, the second fixing post 2212T is a stud, and the second fastener S2 is threadedly connected with the second fixing post 2212T.

In an embodiment, the sealing gasket 250 is defined with an avoidance groove 250C facing the second avoidance groove 240C and the first avoidance groove 230C, and the second fixing post 2212T is partially arranged in the avoidance groove 250C for avoidance.

In an embodiment, the main housing 210 includes a cover plate 210A and a side plate 210B which are connected with each other, the side plate 210B is connected between the performing part 200 and the cover plate 210A, and the electrode assembly 220, the circuit board 230, and the insulating substrate 240 are arranged in a space surrounded by the cover plate 210A and the side plate 210B.

In an embodiment, the performing part 200 of the beauty instrument further includes an annular sealing ring M, and the sealing ring M is sealed between the cover plate 210A and the side plate 210B.

As shown in FIG. 4, the sealing ring M includes:

a body part M1;

a first flange M2 protruded on a surface of the body part M1 facing the side plate 210B; and a second flange M3 protruded on an outer ring surface of the body part M1 and closing to the first flange M2.

An end face of the cover plate 210A facing the side plate 210B is defined with a circle of concave part 210R, and an end face of the side plate 210B facing the cover plate 210A is formed with a convex rib 210Q. The body part M1 and the second flange M3 are arranged in the concave part 210R, and an inner ring face of the body part M1 is abutted against the convex rib 210Q, and the cover plate 210A presses the first flange M2 against the end face of the side plate 210B.

As a main component of the sealing ring M, the body part M1 has an annular structure, the second flange M3 is located on the outer ring surface of the body part M1, and the first flange M2 is located on the end face of the body part M1 and faced the side plate 210B. After the cover plate 210A and the side plate 210B are assembled, the sealing ring M is compressed between the cover plate 210A and the side plate 210B, and an end of the body part M1 facing away from the first flange M2 is pressed against the outer side of the rib 210Q by the inner side wall of the cover plate 210A, the second flange M3 is pressed against the end of the side plate 210B by the end of the cover plate 210A, and the first flange M2 is pressed against the end of the side plate 210B by the body part M1 to form close fit with the end of the side plate 210B. In this way, the sealing ring M, the rib 210Q, and the end of the cover plate 210A cooperate with each other, so that a large sealing contact surface can be formed on a joint surface of the cover plate 210A and the side plate 210B, improving waterproof sealing effect of the joint surface.

Figure 7:
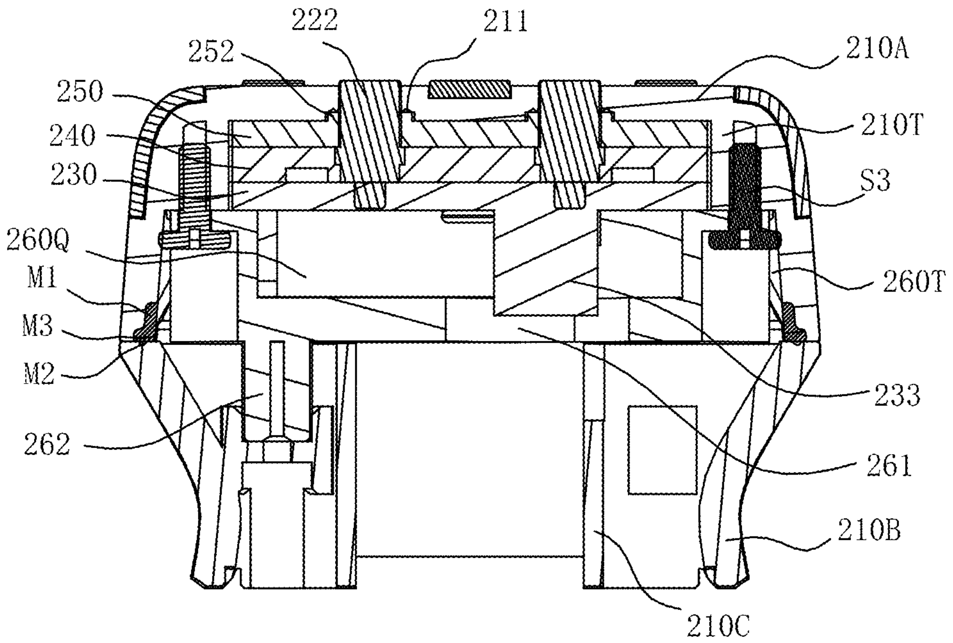
FIG. 7 shows yet another schematic sectional view of operating parts of a beauty instrument according to an embodiment of the present disclosure.
Figure 8:
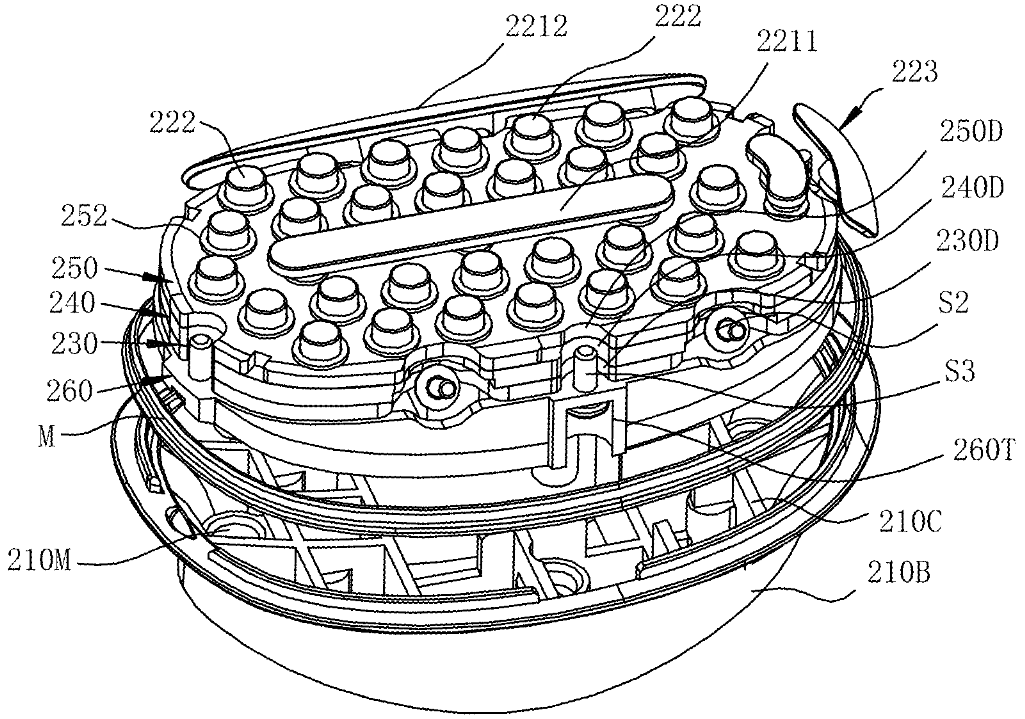
FIG. 8 shows a schematic view of an internal structure of operating parts of a beauty instrument according to an embodiment of the present disclosure.

Further referring to FIGS. 7 and 8, in an embodiment, the performing part 200 includes a fixing frame 260, and the fixing frame 260 is arranged at a side of the circuit board 230 facing away from the electrode assembly 220. The fixing frame 260 is fixed to the inner surface of the end 2101 of the main housing 210 and presses the circuit board 230, the insulating substrate 240, and the sealing gasket 250 in a stack against the inner surface of the end 2101 of the main housing 210.

Illustratively, the performing part 200 includes a third fastener S3, a plurality of third fixing posts 260T are protruded on an edge of the fixing frame 260 and abutted against the circuit board 230, an end of the third fastener S3 penetrate through the third fixing post 260T, and the other end is connected with the inner surface of the end of the main housing 210. The edge of the circuit board 230 is defined with a third avoidance groove 230D corresponding to the third fastener S3, and/or the edge of the insulating substrate 240 is defined with a fourth avoidance groove 240D corresponding to the third fastener S3, and/or an edge of the sealing gasket 250 is defined with a fifth avoidance groove 250D corresponding to the third fastener S3. After the third fastener S3 passes through the third fixing post 260T and is connected with the inner surface of the end 2101 of the main housing 210, the third fastener S3 is located in the corresponding third avoidance groove 230D and/or fourth avoidance groove 240D and/or fifth avoidance groove 250D. The circuit board 230, the insulating substrate 240, and the sealing gasket 250 can be tightly fixed in the main housing 210 by the third fixing post 260T abutting against the edge of the circuit board 230.

In an embodiment, a fourth fixing post 210T is protruded on the inner surface of the end 2101 of the main housing 210, and the third fastener S3 is connected with the fourth fixing post 210T. For example, the fourth fixing post 210T is a stud, and the third fastener S3 is threadedly connected with the fourth fixing post 210T.

Illustratively, after the third fastener S3 is connected with the fourth fixing post 210T, the fourth fixing post 210T is abutted against the edge of the fixing frame 260, for example, the fourth fixing post 210T is abutted against the third fixing post 260T of the fixing frame 260. The assembled third fixing post 260T is abutted against both the third fixing post 260T and the edge of the circuit board 230, that is, by setting a protruding length of the fourth fixing post 210T, the end of the fourth fixing post 210T can be flush with a surface of the circuit board 230 abutted against the fixing frame 260, so that an internal space of the beauty instrument can be fully utilized. In an embodiment, the fixing frame 260 is formed as a recessed groove body facing away from the circuit board 230, and the edge of the groove body is abutted against the edge of the circuit board 230. An installation space 260Q for accommodating electrical components or wires is formed between a bottom of the groove body and the circuit board 230.

Figure 6:
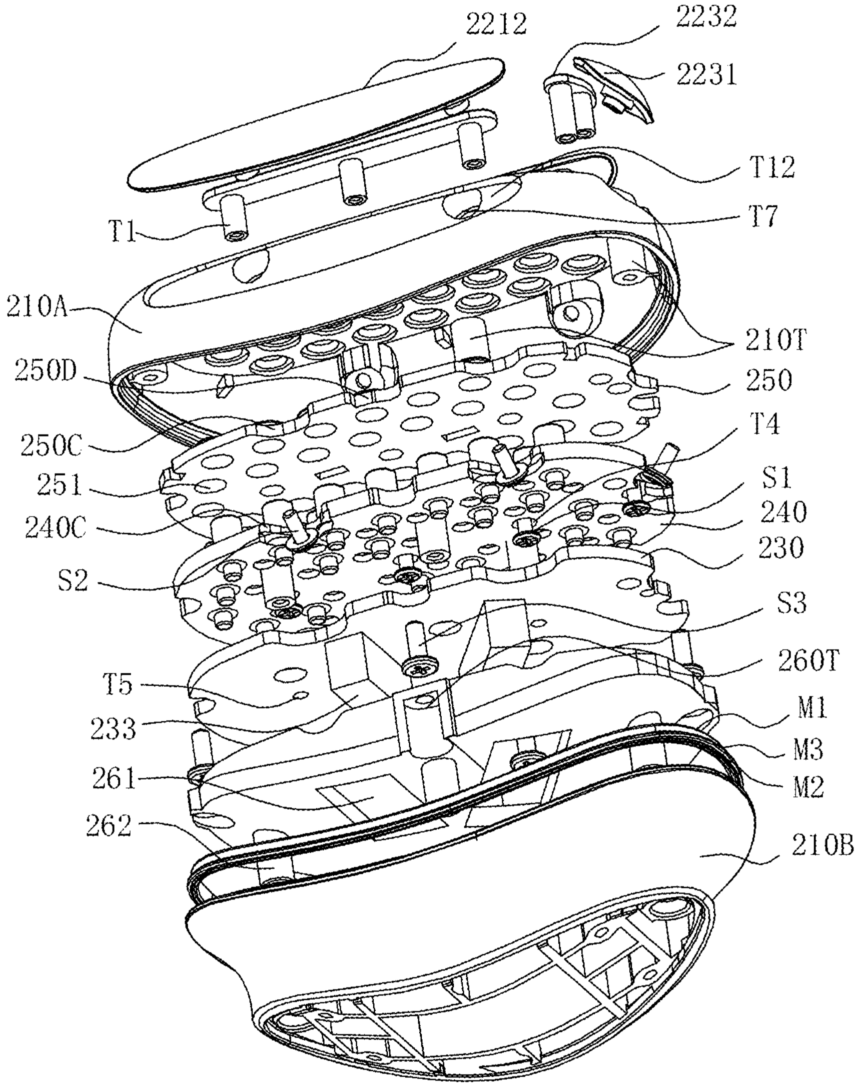
FIG. 6 shows a further schematic exploded view of operating parts of a beauty instrument according to an embodiment of the present disclosure.

As shown in FIGS. 6 to 8, in an embodiment, the circuit board 230 is provided with a protrusion 233 protruding towards the fixing frame 260, the fixing frame 260 is defined with an avoidance hole 261 facing the protrusion 233, and the protrusion 233 is at least partially embedded in the avoidance hole 261. In this way, a part of a structure or components of the circuit board 230 can be accommodated in the avoidance hole 261 of the fixing frame 260, and a gap between the fixing frame 260 and the circuit board 230 does not need to be enlarged, so that the internal space of the beauty instrument can be saved and structural compactness can be improved. Illustratively, the circuit board 230 includes a plurality of protrusions 233, and the fixing frame 260 is correspondingly defined with a plurality of avoidance holes 261 facing the protrusions 233.

In an embodiment, a side of the fixing frame 260 facing away from the cover plate 210A is fixed to the side plate 210B. In particular, as shown in FIG. 4 and FIGS. 6 to 8, a fifth fixing post 262 is protruded on a side of the fixing frame 260 facing away from the cover plate 210A, and a side of the cover plate 210A facing the fixing frame 260 is defined with a counterbore 210M. The fifth fixing post 262 is embedded in the counterbore 210M and is fixed in the counterbore 210M by a fastener (not shown) penetrating from a side of side plate 210B facing away from the fixing frame 260.

Through above arrangement, the fixing frame 260, the insulating substrate 240, and the sealing gasket 250 can be fixed to the inner surface of the end 2101 of the main housing 210, that is, fixed to the cover plate 210A, by the third fastener S3 being loaded from the edge of the fixing frame 260. By inserting another fastener from the side of the side plate 210B facing away from the fixing frame 260 through the counterbore 210M so as to be connected with the fifth fixing post 262 of the fixing frame 260, the fixing frame 260 can be fixed to the side plate 210B, and the sealing ring M can also be compressed, thus enhancing clamping effect of the side plate 210B and the cover plate 210A.

In an embodiment, a side of the side plate 210B facing the fixing frame 260 is provided with a plurality of ribs 210C, the fixing frame 260 is abutted against the ribs 210C, and the ribs 210C can strengthen and limit the fixing frame 260, thus improving structural strength of the performing part 200.

In an embodiment, the beauty instrument includes:

a main housing 210; and an electrode assembly 220 provided in the main housing 210, the electrode assembly 220 including:

a plurality of elongated first electrodes 221, each of the plurality of elongated first electrodes 221 being exposed on the main housing 210, the plurality of elongated first electrodes 221 being arranged at intervals; and a plurality of dot electrodes 222 arranged at intervals, at least part of the dot electrodes 222 being arranged between two adjacent first electrodes 221 in an array, an end of each of the dot electrodes 222 being exposed on the end 2101 of the main housing 210.

In this way, the elongated first electrodes 221 at the two sides are large-area electrodes that act on the skin to discharge, and the dot electrodes 222 between the elongated first electrodes 221 uniformly discharge to the skin on an area between the first electrodes 221, so that user is prevented from obviously feeling the electrode provision area on the care head, discharge uniformity is improved, a care area of the electrodes of the beauty instrument is increased, and care experience and efficiency are also improved. Further, different electrodes can act on the skin in different areas, thereby further expanding application scenes and meeting care needs of different skin areas.

Illustratively, the first electrodes 221 are parallel to each other. That is, extending directions of the first electrodes 221 are the same. When the beauty instrument moves along the skin surface, the elongated first electrodes 221 at the two sides are in contact with the skin at the same time, thus forming a loop and generating a current at a contact site with the skin, for example, a micro current or radio frequency current, to perform skin care.

It can be understood that in other embodiments, the first electrode 221 is not limited to be of a regular strip shape, and for example, the first electrode 221 can also be a wavy, zigzag, or multi-segment connected electrode.

In an embodiment, the first electrodes 221 include a first sub-electrode 2211 and a second sub-electrode 2212, and the first sub-electrode 2211 and the second sub-electrode 2212 have opposite polarities and form an electrode pair. At least part of the dot electrodes 222 are arranged between the first sub-electrode 2211 and the second sub-electrode 2212 in an array, thus filling a blank area between the first sub-electrode 2211 and the second sub-electrode 2212, thus performing care for a target skin area between the first sub-electrode 2211 and the second sub-electrode 2212, expanding a discharge area of the beauty instrument and improving care efficiency.

In an embodiment, the first sub-electrode 2211 is disposed at the end 2101 of the main housing 210 and closing to the middle area of the end 2101 of the main housing, the second sub-electrode 2212 is arranged at an edge of the end 2101 of the main housing 210, and the second sub-electrode 2212 at least partially extends to the side 2102 of the main housing 210.

During the process of the beauty instrument being pushed along the skin surface, the first sub-electrode 2211 and the dot electrodes 222 can serve to perform skin care on a large flat area, for example, by generating a micro current acting, to achieve skin resurfacing effect. The second sub-electrode 2212 can serve to perform care for an uneven skin surface. For example, the second sub-electrode 2212 can be in contact with an edge of the nose to discharge to skin around the nose.

In an embodiment, the first electrodes 221 include two second sub-electrodes 2212, each second sub-electrode 2212 is located at one side edge of two side edges of the main housing 210, the first sub-electrode 2211 is arranged between the two second sub-electrodes 2212, and each of the two second sub-electrodes 2212 and the first sub-electrode 2211 have opposite polarities and form an electrode pair.

When the first sub-electrode 2211 and a corresponding second sub-electrode 2212 at the two sides are in contact with the skin at the same time, they can form a loop and thus discharge to the skin. The second sub-electrodes 2212 at the two sides can perform care for skin in different areas, thus expanding application scenarios.

In an embodiment, dot electrodes 222 in an array are arranged between each of the second sub-electrodes 2212 and the first sub-electrode 2211. Thus, an area between the second sub-electrode 2212 on each side and the first sub-electrode 2211 at the middle can be filled with the dot electrodes 222 to discharge a target area between each of the second sub-electrodes 2212 and the first sub-electrode 2211.

In an embodiment, the electrode assembly 220 further includes a second electrode 223 disposed between the two second sub-electrodes 2212, and the second electrode 223 includes a first arc-shaped electrode 2231 and a second arc-shaped electrode 2232, which have opposite polarities and form an electrode pair. When the first arc-shaped electrode 2231 and the second arc-shaped electrode 2232 are in contact with the skin at the same time, they can form a loop and thus discharge to the skin.

In an embodiment, the first arc-shaped electrode 2231 is arranged at the edge of the end 2101 of the main housing 210, and the first arc-shaped electrode 2231 extends to the side 2102 of the main housing 210. In this way, the first arc-shaped electrode 2231 of the second electrode 223 is located at the edge of the end 2101 of the main housing 210, and can cooperate with the second arc-shaped electrode 2232 to be in contact with an uneven skin surface to discharge.

In an embodiment, the two second sub-electrodes 2212 and the second electrode 223 surround the dot electrodes 222. Therefore, a blank area among the second sub-electrode 2212, the first arc-shaped electrode 2231, and the second arc-shaped electrode 2232 (that is, an area without electrodes) can be filled by the dot electrodes 222, to allow the dot electrodes 222 to discharge to the skin, thus increasing care area.

In an embodiment, dot electrodes 222 are disposed between the edge of the end 2101 of the main housing 210 and at least one end of the first sub-electrode 2211 in a longitudinal direction. In this way, the blank area on a surface of the main housing 210 can be further reduced, thus increasing an effective care area of the beauty instrument.

The above are only specific embodiments of the present disclosure. It should be pointed out that some improvements and modifications can be made by those of ordinary skilled in the art without departing from technical principle of the present disclosure, which should also be regarded to be within a protection scope of the present disclosure.

What is claimed is:

1. A beauty instrument, comprising:

a main housing; and an electrode assembly provided in the main housing, the electrode assembly comprising:

a plurality of elongated first electrodes, each of the plurality of elongated first electrodes being at least partially exposed on the main housing, the plurality of elongated first electrodes being arranged at intervals;

wherein the plurality of elongated first electrodes comprise a first sub-electrode and two second sub-electrodes; wherein the first sub-electrode is arranged at the end of the main housing and closing to a middle area of the end of the main housing;

the two second sub-electrodes are arranged at side edges of the end of the main housing, and at least part of each of the two second sub-electrodes extends to a side of the main housing; and the first sub-electrode is arranged between the two second sub-electrodes, and each of the two second sub-electrodes and the first sub-electrode have opposite polarities and form an electrode pair;

wherein the electrode assembly further comprises:

a second electrode arranged between the two second sub-electrodes and configured in an arc shape;

wherein a curvature center of the second electrode is collinear longitudinally to the first sub-electrode.

2. The beauty instrument according to claim 1, wherein the plurality of first electrodes are parallel to each other.

3. The beauty instrument according to claim 1, wherein the beauty instrument further comprises a plurality of dot electrodes arranged at intervals, and a part of the plurality of dot electrodes are arranged between at least one end of the first sub-electrode in a longitudinal direction and an edge of the end of the main housing in the longitudinal direction of the first sub-electrode.

4. The beauty instrument according to claim 1, wherein an edge of each first electrode is chamfered; and/or two ends of each first electrode in a length direction are arc-shaped; and/or the beauty instrument further comprises a plurality of dot electrodes arranged at intervals, and an edge of each dot electrode is chamfered.

5. The beauty instrument according to claim 1, wherein an edge of the second electrode is chamfered; and/or two ends of the second electrode in a length direction are arc-shaped.

6. The beauty instrument according to claim 1, wherein the second electrode comprises a first arc-shaped electrode and a second arc-shaped electrode.

7. The beauty instrument according to claim 6, wherein the first arc-shaped electrode is arranged at the edge of the end of the main housing, and at least part of the first arc-shaped electrode extends to the side of the main housing.

8. The beauty instrument according to claim 6, wherein the second electrode is disposed at an end of each first electrode along an extending direction of each first electrode.

9. The beauty instrument according to claim 8, wherein the beauty instrument further comprises an operating part connected to the main housing and configured for a user to hold and grip; and each second sub-electrode of the two second sub-electrodes is arranged on one side of two sides of the main housing in a thickness direction of the operating part, the first arc-shaped electrode and the second arc-shaped electrode are located between the two second sub-electrodes and at an end of the first sub-electrode, and the first arc-shaped electrode is further away from the first sub-electrode than the second arc-shaped electrode.

10. The beauty instrument according to claim 6, wherein the second arc-shaped electrode is arranged at an end of the main housing and close to the first arc-shaped electrode; and/or the first arc-shaped electrode and the second arc-shaped electrode extend in a same direction, and the first arc-shaped electrode and the second arc-shaped electrode are arched away from the first sub-electrode; and/or the beauty instrument further comprises an operating part connected to the main housing and configured for a user to hold and grip, and both the first arc-shaped electrode and the second arc-shaped electrode extend toward two sides of the operating part in a thickness direction of the operating part.

11. The beauty instrument according to claim 10, wherein the beauty instrument further comprises a plurality of dot electrodes arranged at intervals, and the two second sub-electrodes and the second electrode surround the plurality of dot electrodes.

12. The beauty instrument according to claim 6, wherein the first arc-shaped electrode and the second arc-shaped electrode have opposite polarities and form an electrode pair.

13. The beauty instrument according to claim 1, further comprising:

an operating part, connected to the main housing and configured for a user to hold and grip;

wherein an extending direction of each first electrode is perpendicular to a thickness direction of the operating part.

14. The beauty instrument according to claim 13, wherein the operating part is flat in shape, and a length direction of the operating part is perpendicular to the thickness direction of the operating part; and the operating part is provided with two grip parts, and each grip part is arranged on a flat surface on one side of two sides of the operating part in the thickness direction of the operating part.

15. The beauty instrument according to claim 14, wherein each grip part comprises a concave part formed on a side of the operating part, and the concave part extends along a length direction of each first electrode.

16. The beauty instrument according to claim 1, wherein the electrode assembly further comprises:

a plurality of dot electrodes arranged at intervals, the plurality of dot electrodes arranged in an array are arranged between each of the two second sub-electrodes and the first sub-electrode.

17. The beauty instrument according to claim 16, wherein the plurality of dot electrodes comprises a plurality of rows of dot electrodes, and two adjacent dot electrodes among each row of dot electrodes have opposite polarities and form an electrode pair.

18. The beauty instrument according to claim 16, wherein an area of the first arc-shaped electrode and an area of the second arc-shaped electrode are both larger than an area of the dot electrode.

19. The beauty instrument according to claim 16, wherein the plurality of dot electrodes are arranged between the second arc-shaped electrode and the first sub-electrode.

* * * * *